United States Patent [19]

Labarde

[11] Patent Number: 4,583,945
[45] Date of Patent: Apr. 22, 1986

[54] TISSUE PROTECTION DEVICE FOR MOUNTING ON THE HEAD OF A DENTIST'S DRILL

[76] Inventor: Bernard Labarde, 87330 Mezieres-sur-Issoire, France

[21] Appl. No.: 704,187

[22] Filed: Feb. 22, 1985

[30] Foreign Application Priority Data

Feb. 22, 1984 [FR] France .................. 84 02679

[51] Int. Cl.⁴ .............................................. A61C 1/16
[52] U.S. Cl. ................................................ 433/116
[58] Field of Search ......................................... 433/116

[56] References Cited

U.S. PATENT DOCUMENTS

| 787,981 | 4/1905 | Green ................... 433/116 |
| 2,671,269 | 3/1954 | Francis .................. 433/116 |
| 2,924,013 | 2/1960 | Wowra ................... 433/116 |

FOREIGN PATENT DOCUMENTS

| 139792 | 1/1980 | Fed. Rep. of Germany ...... 433/116 |
| 602086 | 7/1978 | Switzerland ................. 433/116 |

*Primary Examiner*—Robert Peshock
*Attorney, Agent, or Firm*—Gerald J. Ferguson, Jr.

[57] ABSTRACT

A device for protecting tissue and capable of being mounted on the head of a dentist's drill. Means (1') for mounting the device on the head of a dentist's drill carry a body (2') which is rotatable about a longitudinal axis which coincides with the axis of the drill in the working position, and the body (2') carries a housing (3') for a rod (6) which is connected via a hinge (7) to a tilting portion of a protective plate (4).

6 Claims, 6 Drawing Figures

TISSUE PROTECTION DEVICE FOR MOUNTING ON THE HEAD OF A DENTIST'S DRILL

The invention relates to a device for protecting soft tissues inside the mouth while performing dental work by means of a drill or like tool which is caused to rotate at a suitable speed, for example by an air turbine.

BACKGROUND OF THE INVENTION

Published French Pat. No. 2 228 463 describes a device of this type for mounting on the bend in the grip or handle of the turbine in a dentist's drill, and comprises a fixing hook together with a protective wall. The wall pivots relative to the fixing hook about a geometrical axis which is parallel to the axis of the drill when in use. When drilling a tooth, it is necessary to be able to work on both of the free sides of a tooth, i.e. on the cheeck side and on the tongue side. It is also necessary to be able to work on the sides close to the adjacent teeth. In such a case, the known device abuts against the adjacent teeth. It has to. be removed before working between teeth with the drill. It has even appeared that this known protector can be used on the tongue side of a tooth only for drilling the middle of said tongue side, since the width of the protective wall causes it to encounter the adjacent tooth well before the drill arrives in the proximity of said adjacent tooth.

A main object of the invention is to provide a protection device of the above-described type for protecting soft tissues, but which enables any point on the side of a tooth to be drilled from close proximity to a first adjacent tooth to close proximity to a second adjacent tooth at the opposite end of the tooth being drilled.

SUMMARY OF THE INVENTION

In a protective device fitted with means for mounting on a dentist's drill head and with a protective plate in accordance with the invention, the protective plate comprises a fixed portion and a tilting portion, the tilting portion being connected to the fixed portion via a hinge which is disposed in the assembly transversely to the longitudinal dimension of the plate which plate is parallel to the drill in the mounting position of the drill head.

In accordance with a second characteristic of the invention, the fixed portion of the plate is connected to the mounting means via a body, which body is advantageously provided with a cylindrical housing having an axis which is generally parallel to the axis of the drill in the working position and the fixed portion of the plate is provided with a rod suitable for being housed in said housing.

In accordance with the first aspect of the invention, the body is fixed relative to the mounting means; the rod is cylindrical and it is a push fit in the corresponding housing with the possibility of rotating about the general axis of said housing.

In accordance with a second aspect of the invention, the body is mounted to be rotatable relative to the mounting means about a geometrical axis which is very near the general axis of the drill in its working position.

In a preferred embodiment of the invention, the hinge which connects the fixed portion of the plate to the tilting portion thereof includes a stop preventing tilting in one direction and a return spring for resisting tilting in the other direction.

The protective plate has at least one of its main faces polished like a mirror.

BRIEF DESCRIPTION OF THE DRAWINGS

Two embodiments of the invention are described by way of example with reference to the accompanying drawings, in which.

DESCRIPTION OF PREFERRED EMBODIMENTS

Figure 1:
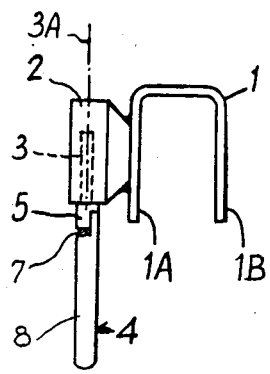
FIG. 1 is a front view of a protective device in accordance with the invention.
Figures 2, 7:
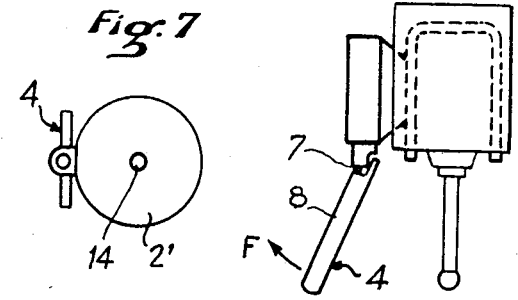
FIG. 2 is a view similar to FIG. 1 showing the device mounted on the head of a dentist's drill.
FIG. 7 is a plan view of the device shown in FIG. 6.
Figure 3:
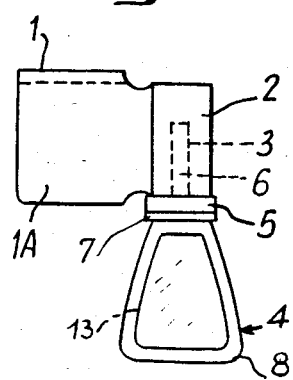
FIG. 3 is a side view of the same device.

In the embodiment shown in FIGS. 1 to 3, the mounting means is constituted by a bracket 1 having two parallel branches 1A and 1B. The bracket 1 slides over the head of a dentist's drill as shown in FIG. 2.

Figure 6:
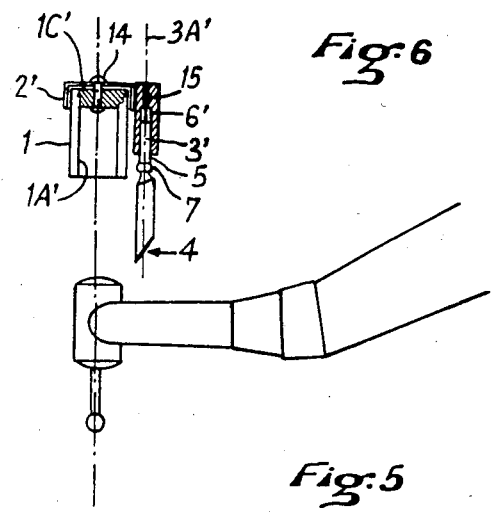
FIG. 6 is an elevation view of a variant embodiment of a protective device in accordance with the invention shown partially in section and ready for mounting on a dentist's drill head.

In the embodiment shown in FIGS. 6 and 7, the mounting means is a cap 1' having a side opening 1A' and suitable for sliding over the head of a dentist's drill, as shown in FIG. 6.

In the embodiment of FIGS. 1 to 3, the outside face of the branch 1A is fitted with a fixed body 2 which extends laterally to come close to the drill head. A cylindrical housing 3 is provided in the body 2 and has a general axis 3A which is parallel to the general axis of the drill in its position of use.

The cylindrical housing 3 serves to receive a protective plate 4 which comprises a fixed portion 5 and a tilting portion 8. The fixed portion 5 is fitted with a cylindrical rod 6. The rod is a push fit in the housing 3 but enables the plate 4 to be oriented in any desired direction by forcing the rod 6 to rotate about the general axis 3A inside the housing 3 and against the friction between the rod and the housing.

In the example shown in FIGS. 6 and 7, the mounting means is the cap 1' which is provided on its end face 1C' with a rotating body 2' which extends laterally over the side of the cap 1' and which has a housing 3' having a general axis 3A'. The axis 3A' is parallel to the general axis of the drill when the cap 1' is mounted on the head of a dentist's drill. The housing 3' is intended for mounting the protective plate 4. The protective plate is made in exactly the same way as has been described with reference to FIGS. 1 to 3. It thus likewise includes a fixed portion 5 fitted with a rod 6. The rod is mounted in the housing 3' and is capable of sliding axially therein against the force of a spring as is explained in greater detail below.

In both embodiments, the fixed portion 5 of the plate is connected via a hinge 7 to the tilting portion 8 which constitutes the protective portion per se of the plate. The tilting portion extends parallel to the drill in the working position in the direction of its longitudinal dimension as can be seen in FIGS. 2 and 6. The hinge 7 is transversal to said longitudinal dimension.

Figure 4:
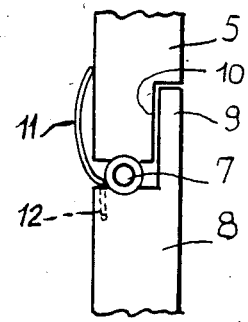
FIG. 4 is a view on a larger scale showing a portion of the protective plate in the vicinity of the hinge connecting the fixed and tilting portions thereof.

The tilting portion 8 is provided with a lip (FIG. 4) extending beyond the hinge 7 towards the fixed portion 5 and occupying a corresponding recess 10 provided therein in the face which faces the drill. This provides a stop preventing the tilting portion 8 from tilting into the drill. The recess 10 means that the hinge 7 must be offset in the thickness of the protective plate 4. It may be observed that a recess 10 is not strictly necessary and that some other type of stop could be adopted. It is advantageous to provide resilient return means between the fixed portion 5 and the tilting portion 8, which return means could be incorporated in the hinge 7. In the example shown the return means is constituted by a flat spring 11 inserted in a slot 12 in the tilting portion 8 and extending over the fixed portion 5 on the side thereof facing away from the drill. Thus, the protective plate 4 can only tilt away from the drill as indicated by an arrow F in FIG. 2. The resilient return means 11 tend to return the plate to the position in which is parallel to the drill.

In accordance with the invention, the inside face of the protective plate 4 (i.e. the face turned towards the drill in the working position), or of at least the tilting portion 8 of the protective plate is reflecting or is provided at least partially with a reflecting layer 13. Thus, while drilling a tooth, the user may observe the drilled zone as reflected by said face of the plate 4.

In the present description, it should be understood that the portion of the plate is referred as the "fixed" portion in relative terms since it is more fixed than the tilting portion 8.

In the first embodiment shown in FIGS. 1 to 3, the protective plate 4 is rotatable about the axis 3A which is parallel to the general axis of the drill. The specific direction in which it points is determined by rotating the rod 6 in the housing 3. In addition, the rod 6 may be removed from the housing 3 by applying sufficient axial force thereto. In this example, the protective plate 4 is easily replaced. It may be discarded after use.

In the second embodiment described with reference to FIGS. 6 and 7, the body 2' is fitted over the top of the cap 1' and it is connected thereto about the central axis 14. The body 2' may be crimped, for example, to the end face of the cap 1'. The central axis 14 substantially coincides with the general axis of the drill in the working position. In this position, the axis 3A' is substantially parallel to the general axis of the drill. The assembly comprising the moving body 2', the housing 3' and the plate 4 may be turned about the general axis of the drill through about 230°. The rod 6 of the fixed portion 5 of the plate 4 is mounted in the housing 3 and is capable of sliding axially therein. For example, a compression spring 15 is disposed in the housing 3' to press against the end of the housing 3' and against the leading end of the rod 6 (not visible in FIG. 6). In this second example, the rod 6 may be fixed or it may be rotatable in the housing 3' about the axis 3A'. The plate 4 is for permanent use, but it is also possible to provide for easy disassembly of the rod 6 from the housing 3' so that the plate 4 can be replaced after each use.

Figure 5:
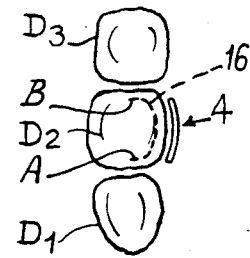
FIG. 5 is a diagram showing three teeth for explaining the advantages of the invention.

FIG. 5 shows three successive teeth D1, D2, and D3. In order to fix a prosthesis to the middle tooth D2, it is necessary to remove its entire perimeter to leave the central portion thereof. The drilling operation performed in this case is essentially a milling operation. On each side of the middle tooth, the drilling operation extends between a point A close to the tooth D1 and a point B close to the tooth D3 and extends along a path 16 shown in dashed lines on the tongue side of the tooth shown. While the middle portion of the path 16 is being drilled, the protective plate 4 is parallel to the tooth and prevents any accidental contact between the tongue and the tooth or the drill. As the drill moves closer to one or other of the adjacent teeth D1 and D3, the plate 4 encounters one or other tooth and lifts as shown in FIG. 2, thus enabling the drill to continue to engage the middle tooth without interruption over the entire path between points A and B.

I claim:

1. A device for protecting an inner portion of a patient's mouth from a dentist's drill where said drill includes a drill head, said device comprising;
   a protective plate having a fixed portion and a tilting portion pivotally mounted with respect to the fixed portion such that the protective plate may be pivoted away from or toward the drill;
   mounting means for mounting the fixed portion with respect to the drill head; and
   spring means for biasing said tilting portion to a first predetermined position, said tilting portion being movable toward a second predetermined position against the bias of said spring means upon insertion of said tilting portion between a tooth of a patient and said inner portion of patient's mouth to be protected, said tilting portion being biased toward said tooth, which substantially corresponds to said first predetermined position whereby said drill head may be positioned at different orientations with respect to said tooth while the tilting portion remains substantially fully in position between the tooth and inner portion of the mouth to be protected due to the spring biased, pivotal mounting of the tilting portion with respect to the fixed portion of the protective plate.

2. A device as recited in claim 1 where said drill has an axis and where said mounting means includes a cylindrical housing means having an axis substantially parallel to the axis of the drill and said fixed portion of the protective plate includes a rod member which is push fit into said cylindrical housing whereby said rod may be rotated about the axis of said cylindrical housing against the friction of the push fit to thus permit rotation of said protective plate about the axis of the rod.

3. A device as recited in claim 2 including a body having an axis of symmetry and being rotatably mounted about its axis symmetry with respect to said mounting means where said axis of the body is substantially colinear with the axis of said drill, said cylindrical housing being attached to said body whereby said protective plate may additionally be rotated about the axis of the drill.

4. A device as recited in claim 3 where said cylindrical housing contains a spring therein which presses said rod of said fixed portion of the protective plate against said push fit allowing sliding movement of said rod within said cylindrical housing whereby said protective plate may additionally undergo movement along the axis of said rod.

5. A device as recited in claim 1 including a body having an axis of symmetry and being rotatably mounted about its axis of symmetry with respect to said mounting means where said axis of said body is substantially colinear with the axis of the drill, said fixed portion of the protective plate being attached to said body whereby said protective plate may additionally undergo rotative movement with respect to said drill.

6. A device as recited in claim 1 where at least one face of said tilting portion of the protective plate has a light reflective surface.

* * * * *